US008586107B2

(12) United States Patent
Garnier et al.

(10) Patent No.: US 8,586,107 B2
(45) Date of Patent: Nov. 19, 2013

(54) SCHISANDRA SPHENANTHERA FRUIT EXTRACT AND COSMETIC, DERMATOLOGICAL, AND NUTRACEUTICAL COMPOSITIONS COMPRISING SAME

(75) Inventors: Sebastien Garnier, Pierres (FR); Philippe Msika, Versailles (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 13/387,524

(22) PCT Filed: Jul. 27, 2010

(86) PCT No.: PCT/EP2010/060873
§ 371 (c)(1),
(2), (4) Date: Jan. 27, 2012

(87) PCT Pub. No.: WO2011/012612
PCT Pub. Date: Feb. 3, 2011

(65) Prior Publication Data
US 2012/0121743 A1    May 17, 2012

(30) Foreign Application Priority Data

Jul. 30, 2009   (FR) ...................................... 09 55344

(51) Int. Cl.
*A61K 36/00* (2006.01)
*A61K 36/79* (2006.01)
*A61K 38/00* (2006.01)

(52) U.S. Cl.
USPC ............................. 424/725; 424/777; 514/1.1

(58) Field of Classification Search
None
See application file for complete search history.

(56) References Cited

U.S. PATENT DOCUMENTS

| 5,484,595 A | 1/1996 | Ikeya et al. | |
|---|---|---|---|
| 2003/0026854 A1* | 2/2003 | Zhao ............................. | 424/725 |

FOREIGN PATENT DOCUMENTS

| CN | 1120409 A | * | 4/1996 |
|---|---|---|---|
| CN | 1846762 A | * | 10/2006 |
| FR | 2822821 | | 10/2002 |
| FR | 2857596 | | 7/2003 |
| FR | 2910815 | | 7/2008 |
| WO | WO 98/47479 | | 10/1998 |
| WO | WO 01/21150 | | 3/2001 |
| WO | WO 01/21605 | | 3/2001 |
| WO | WO 01/51596 | | 7/2001 |
| WO | WO 01/52837 | | 7/2001 |
| WO | WO 02/06205 | | 1/2002 |
| WO | WO 2004/012496 | | 2/2004 |
| WO | WO 2004/012752 | | 2/2004 |
| WO | WO 2004/016106 | | 2/2004 |
| WO | WO 2004/050052 | | 6/2004 |
| WO | WO 2004/050079 | | 6/2004 |
| WO | WO 2004/112741 | | 12/2004 |
| WO | WO 2004/112742 | | 12/2004 |
| WO | WO 2005/044289 | | 5/2005 |
| WO | WO 2005/102259 | | 11/2005 |
| WO | WO 2005/105123 | | 11/2005 |
| WO | WO 2005/115421 | | 12/2005 |
| WO | WO 2006/122454 | | 11/2006 |
| WO | WO 2006/122485 | | 11/2006 |
| WO | WO 2007/005760 | | 1/2007 |
| WO | WO 2007/020382 | | 2/2007 |
| WO | WO 2007/057439 | | 5/2007 |
| WO | WO 2008/009709 | | 1/2008 |
| WO | WO 2008/080974 | | 7/2008 |

OTHER PUBLICATIONS

Yamasaki, Kenshi and Gallo, Richard, "The molecular pathology of rosacea," J Dermatol Sci., Aug. 2009, vol. 55, No. 2, pp. 77-81.
Yue, J. et al., "Ganschisandrine, A Lignan From *Schisandra sphenanthera*," Phytochemistry, 1989, vol. 28, No. 6, pp. 1774-1776.
Yue, J. et al., "Triterpenoids of *Schisandra sphenanthera*," Phytochemistry, 1994, vol. 35, No. 4, pp. 1068-1069.
Zhu, M. et al., "Variation of the Lignan Content of *Schisandra chinensis* (Turcz.) Baill. and *Schisandra sphenanthera* Rehd. et Wils.," Chromatographia, Jul. 2007, vol. 66, No. ½., pp. 125-128.
Liu, C. et al., "Studies on the Active Principles of *Schisandra sphenanthera* Rehd. et Wils.," Scientia Sinica, Jul.-Aug. 1978, vol. XXI, No. 4, pp. 483-502.
Song, L. et al., "Compositions and Biological Activities of Essential Oils of *Kadsura longepedunculata* and *Schisandra spenanthera*," The American Journal of Chinese Medicine, 2007, vol. 35, No. 2, pp. 353-364.
Wang, J. et al., "Development of a quality evaluation method for *Fructus schisandrae* by pressurized capillary electrochromatography," J. Sep. Sci. 2007, vol. 30, pp. 381-390.
Jiang, S. et al., "Sphenanlignan, a New Lignan from the Seeds of *Schisandra sphenanthera*," Chin. J. Nat. Med., Mar. 2005, vol. 3, No. 2, pp. 78-82.
Ikeya, Y. et al., "Two Lignans From *Schisandra sphenanthera*," Phytochemistry, 1991, vol. 30, No. 3, pp. 975-980.
Ikeya, Y. et al., "Benzoylgomisin Q and Benzoylgomisin P, Two New Lignans from *Schisandra sphenanthera* Rehd. et Wils.", Chem. Pharm. Bull., 1990, vol. 38, No. 5, pp. 1408-1411.
Huyke, C. et al., "Composition and Biological Activity of Different Extracts from *Schisandra sphenanthera* and *Schisandra chinesis*," Planta Med., Jul. 5, 2007, vol. 73, pp. 1116-1126.
He, X. et al., "Analysis of lignan constituents from *Schisandra chinensis* by liquid chromatography—electrospray mass spectrometry," Journal of Chromatography A, 1997, vol. 757, pp. 81-87.
Hancke, J., et al., "*Schisandra chinensis* (Turcz.) Baill," Fitoterapia, 1999, vol. 70, pp. 451-471.

(Continued)

*Primary Examiner* — Qiuwen Mi
(74) *Attorney, Agent, or Firm* — Foley & Lardner LLP

(57) ABSTRACT

A cosmetic, dermatological or nutraceutical composition including a *Schisandra sphenanthera* fruit peptide and sugar extract, a crude oil, a refined oil, a refined oil concentrate, and/or the unsaponifiable fraction of the concentrate. A method for preparing a peptide and sugar extract, a refined oil, and/or a concentrate and an unsaponifiable fraction of oil of the *Schisandra sphenanthera* fruit.

5 Claims, No Drawings

(56) References Cited

OTHER PUBLICATIONS

Brown, David A., "Skin pigmentation enhancers," Journal of Photochemistry and Photobiology B: Biology, 2001, vol. 63, pp. 148-161.

Quirin, K.W., "Flavex naturextrakle GmbH, Supercritical Schisandra Extracts—a New Concept for Personal Care Cosmetics," Cosmetic Science Technology, 2008, XP002576906, pp. 29, 31, 33, 35.

International Search Report mailed Feb. 13, 2012 in Int'l Application PCT/EP2010/060873 (3 pages).

French Preliminary Search Report mailed May 4, 2010 in Patent Application FR0955344 (2 pages).

"Schisandrafruchte CO2 to extract varietat sphenanthera, Typ Nr. 164.001," Flavex Naturextrakte GmbH, Version 66.235.02, Mar. 15, 2006, available at www.flavex.com/fileadmin/flavex.de/user_upload/Spezifikation/Deutsch/Spezi_Schisandrafruechte_CO2-to_Extrakt_164_001.pdf (accessed Apr. 7, 2010).

Yang, et al., China Journal of Chinese Materia Medica, Nov. 2001, vol. 26, No. 11, pp. 755-757.

K2E-PAT Machine translation of KR2002-0001931 obtained from http://enq.kipris.or.kr on Mar. 27, 2012 (13 pages).

* cited by examiner

SCHISANDRA SPHENANTHERA FRUIT EXTRACT AND COSMETIC, DERMATOLOGICAL, AND NUTRACEUTICAL COMPOSITIONS COMPRISING SAME

The invention relates to a cosmetic, dermatological or nutraceutical composition comprising a suitable excipient and a *Schisandra sphenanthera* extract.

The *Schisandra sphenanthera* Plant

With the botanical name *Schisandra*, this plant belongs to the class Magnoliopsida and the order Magnoliales. The botanical family is that of Schisandraceae. The complete Latin name is *Schisandra sphenanthera* Rehd. et Wils. The common names of the plant are: schisandre à fleurs orangées (in France), southern *Schisandra* and lemon wood (in England), and hua zhong wu wei zi and nan wu wie zi (in China).

These shrubs originate in northern China and adjacent regions in Russia and Korea. There are about 25 species in the world belonging to the genUS *Schisandra*. Approximately 16 of these are Chinese. Two species are officially recognized as medicinal in China, *S. chinensis* and *S. sphenanthera* (He et al., 1997). Their berries are used in traditional Chinese medicine to treat coughs, asthma, night sweats, nocturnal emissions and chronic diarrhea. They are also used as tonics and to treat chronic fatigue.

The term *Schisandra* used alone may refer to two different plants, *Schisandra chinensis* and *Schisandra sphenanthera*. These two species have long been regarded as equivalent: they could be designated according to their origin, "northern *Schisandra*" for *Schisandra chinensis* and "southern *Schisandra*" for *Schisandra sphenanthera*.

*Schisandra* is a dioecioUS plant (with distinct male and female flowers). The fruit is in the form of a hanging cluster somewhat similar to that of the currant bush. It has a naked peduncle in its upper part (roughly 5-10 cm) that is covered in its lower part by bright red berries which are slightly larger, more compact and firmer than currants. The spherical seed is a few millimeters in size.

Characteristics of the Fruit

Although the fruit of *S. chinensis* has been the subject of an abundance of literature (traditional use, chemical compositions, pharmacological and dermatological effects: see in particular WO 2005/044289), much less work has been done on *S. sphenanthera*. Several reasons explain this discrepancy:
- a poorer reputation in terms of its use according to Chinese tradition,
- a near absence of use in the West,
- a lower proportion of total neolignans compared with *S. chinensis*.

However, commercially, the fruit of *S. sphenanthera* is regarded as less costly than that of *S. chinensis*.

*S. sphenanthera* fruit is characterized by its high deoxyschisandrin content. In contrast, its schisandrin and γ-schisandrin contents are very low compared with those of *S. chinensis* seed (Zhu et al., 2007). Recently, an article by Huyke et al. (2007) reported a comparative study of the effects on cell proliferation of *S. chinensis* and *S. sphenanthera* extracts.

The dry fruit of *Schisandra* comprised approximately 20% essential oils, including 7% to 30% unsaponifiables (Huyke et al., 2007). Lignans are contained in the unsaponifiable fraction of the oils. Other active constituents include phytosterols and vitamins C and E.

Essential Oil (Monoterpenes and Sesquiterpenes)

The essential oil is rich in sesquiterpene derivatives (Song et al., 2007):

δ-cadinene: 25.6%,

γ-cadinene,

β-himachalene, santalol.

The essential oil of *S. chinensis* fruit contains more monoterpene hydrocarbons than that of *S. sphenanthera* fruit (Huyke et al., 2007).

Steroids

Sitosterol (Huyke et al., 2007) (<0.1% in the fruit)

Triterpene Alcohol

Schisanol (I) (Yue et al., 1994)

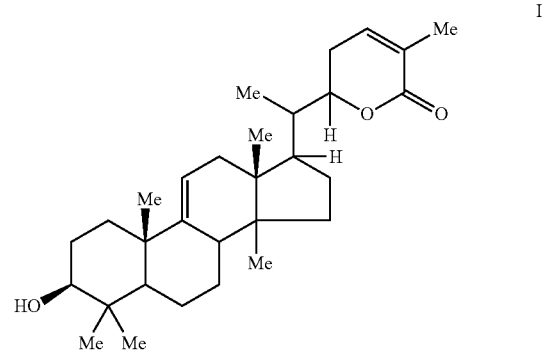 [SMILES: CC1=CCC(C(C)C2CCC3(C)C4CCC5C(C)(C)[C@@H](O)CC[C@]5(C)C4=CC[C@]23C)OC1=O]

Lignans

A. Qualitative Data

Lignans are considered to be the active agents of the fruit for dermatological, cosmetic or pharmaceutical applications. More than 40 dibenzo[a,c]cyclooctadiene-skeleton neolignans, more or less esterified by organic acids (acetic, benzoic, angelic or tiglic acid), have been discovered in *Schisandra* fruits. These are novel components. A general structure of lignans is as follows:

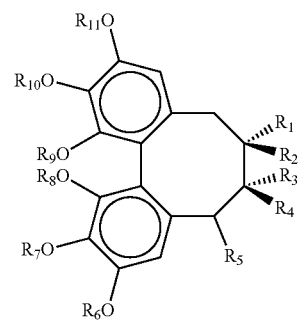

Deoxyschisandrin: $R_{1,3,5}=H$; $R_{2,4,6-11}=CH_3$

The list of neolignans identified in *Schisandra sphenanthera* fruit is presented in table I. For their structures, see the publications by Hancke et al., 1999; He et al., 1997; and Huyke et al., 2007.

TABLE I

| Compounds | Ref. |
|---|---|
| Major | |
| deoxyschisandrin (=wuweizisu = schisandrin A) | (1, 2, 3) (great majority) |
| schisantherin C | (1) |
| "schisantherin" for Zhu et al. (but an isomer of gomisin C) | (3) |
| Minor | |
| schisandrin (=schisandrol A) | (3) (undoubtedly traces) |
| γ-schisandrin (=wuweizisu B = schisandrin B) | (1, 2, 3) (traces) |
| gomisin C (=schisantherin A) | (1, 4) |
| gomisin B (=schisantherin B) | (1) |
| schisantherin D | (1, 4) |
| schisantherin E | (1) |
| gomisin O | (2) |
| deangeloylgomisin B | (2) |
| benzoylgomisin U (I) | (5) |
| tigloylgomisin O (II) | (5) |
| gomisin U | (5) |
| epigomisin | (5) |
| benzoylgomisin Q (III) | (6) |
| benzoylgomisin P (IV) | (6) |
| angeloylgomisin P | (6) |
| tigloylgomisin P | (6) |
| (+)-gomisin K3 | (4) |

(1): Liu et al., 1978;
(2): Huyke et al., 2007;
(3): Zhu et al., 2007;
(4): Yue et al., 1994;
(5): Ikeya et al., 1991;
(6): Ikeya et al., 1990

A diarylbutane lignan called sphenanlignan (I) has been identified in the seed of the fruit (Jiang et al., 2005) and has the following structure:

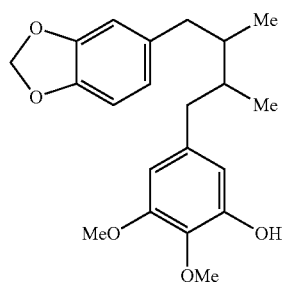

I

B. Quantitative Data

Analyses carried out by TLC-densitometry on 10 species of Schisandra revealed differences in chromatographic profiles between species (Wang et al., 1991). There are several datasets from HPLC analyses of S. sphenanthera neolignans, for example: Zhou et al., 2005.

Table II below presents the major neolignan contents S. sphenanthera fruit, according to articles published in English.

TABLE II

| Compounds | Contents (in mg/g) in the dry fruit according to: | | |
|---|---|---|---|
| Reference | Huyke et al., 2007 (*) | Zhu et al., 2007 | Wang et al., 2007 |
| deoxyschisandrin | 5.1 | 1.5-4.0 | 8.1-13.1 |
| "schisantherin" (**) | | 0.8-3.5 | |
| schisantherin C | | | 1.3-5.8 |
| Gomisin O | 0.9 | | |
| deangeloylgomisin B | 0.6 | | |
| schisandrin | 0.1 | 0.06-0.67 | 0 |
| γ-schisandrin | 0.03 | 0 | 0 |

(*): results by extrapolation of an ethanol extract
(**): naming incomplete; isomeric structure of schisantherin A S. sphenanthera fruit is characterized by its high deoxyschisandrin content. In contrast, its schisandrin and γ-schisandrin contents are very low compared with those of S. chinensis seed (Zhu et al., 2007).

Fruit Extracts: Forms Used

In addition to its traditional use in China in a dehydrated state, Schisandra sphenanthera fruit is also used in the form of extracts obtained by extraction solvents enabling entrainment of the fruit's neolignans. The solvents mentioned in the literature are ethanol, supercritical $CO_2$ ($SC-CO_2$), combined with a cosolvent or not, and hexane.

Several published studies attempted to compare the extractive capacities of $SC-CO_2$, chloroform and 50% methanol and ethanol with regard to fruit neolignans.

According to a recent publication, extraction of S. sphenanthera fruit by $CO_2$ or $CO_2$+5% ethanol, or by hexane, leads to extract compositions that are quite similar in terms of neolignans. In contrast, the use of ethanol led to poorer extraction of two neolignans (dehydroschisandrin and gomisin O) and apparently better extraction of γ-schisandrin (Huyke et al., 2007).

Optimum $SC-CO_2$ extraction conditions for S. sphenanthera fruit neolignans (deoxyschisandrin, γ-schisandrin, etc.) have been proposed in the article by Yang (2001): 21 MPa, 37° C. and a $CO_2$ flow rate of 5 l/min.

Physiopathology of Erythro-couperose and Rosacea

Rosacea is a common dermatosis that primarily affects the face and is seen as a flushed appearance (vasomotor flashes), a permanent erythema, papules, pustules and telangiectasias. Secondary criteria may often appear as sensations of burning or stinging, red patches, cutaneous dryness, facial edema and phymas and ocular manifestations.

This dermatosis may be triggered and aggravated by many factors such as: hot beverages, alcohol, temperature changes, spicy food, exercise, stress and strong emotions, the sun, etc.

The physiopathology of rosacea has long been defined as poorly understood and multifactorial (genetic, inflammatory and vascular factors).

Recently, the involvement of various mechanisms in the initiation of rosacea was discovered and demonstrated (Yamasaki K. & Gallo R L., 2009):

1) altered innate immunity: variants of cathelicidin (LL37) are present in higher quantities than normal; moreover, these variants have inflammatory properties and induce IL-8 secretion;
2) vascular disorders: neoangiogenesis results in telangiectasias (small visible vessels); repeated vasomotor reactions cause lesions of the lymphatic system which are responsible for persistent inflammation;
3) microbial action;
4) oxidative stress and the sun.

These various mechanisms are interrelated. In particular, cathelicidins may also trigger vascular disorders.

Prior Art

No information in the literature concerning the industrial use of *S. sphenanthera* was found. It seems that the fruit of this species has not been exploited for the isolation of neolignans, despite a patent in the United States of America (U.S. Pat. No. 5,484,595).

Medicinal Use:

Application WO 2007/020382 by Phynova describes a composition comprising the extracts of four plants including *Schisandra chinensis* or *Schisandra sphenanthera*, for the treatment of hepatic, metabolic and/or immune disorders, and more particularly intended to treat hepatitis C.

Applications WO 2006/122485 and WO 2006/1222454 by Guang Zhou Zhongyi Pharmaceutical describe compositions intended to treat diabetes, comprising mixtures of several plants including *Schisandra sphenanthera*.

The application US 2003/0026854 by Mr. Zhao describes a schisandrin-based drug for treating liver diseases; the schisandrin is extracted in particular from *Schisandra chinensis* or *Schisandra sphenanthera*.

Application WO 2007/005760 describes a composition comprising compounds of the family of schisandrins, gomisins and other compounds arising from *Schisandra chinensis* and *Schisandra sphenanthera* fruit extracts to treat chemotherapy-resistant cancer cells.

In Europe, no drug authorized by the competent authorities contains *Schisandra sphenanthera* extract. It is generally accepted that *S. sphenanthera* is medicinally inferior to *S. chinensis* and that it is useful only as an alternative source of active lignans.

Dermatological and Cosmetic Use:

An article by Huyke et al. (2007) describes and compares the effects of *S. sphenanthera* and *S. chinensis* extracts on cells in culture: the proliferation of HaCaT and A431 epidermal cells is inhibited in a dose-dependent manner by these extracts, with the nonpolar extracts being more effective than the polar extracts. The $SC-CO_2$ extract of *Schisandra sphenanthera* proved to be the most active with an $IC_{50}$ of 20 µg/ml. In an enzyme inhibition test with free cells, the $SC-CO_2$ extract strongly inhibited prostaglandin production by cyclooxygenase-2 (recombinant COX-2) ($IC_{50}=0.2$ µg/ml compared to 1 µg/ml for indomethacin). It also reduced $PGE_2$ production induced by ultraviolet B rays ($IC_{50}=4$ µg/ml) and COX-2 expression in HaCaT keratinocytes. The authors of the study conclude that the $SC-CO_2$ extract of *Schisandra sphenanthera* could be useful in the prevention and treatment of inflammatory and hyperproliferative diseases of the skin.

The use of *Schisandra chinensis* extracts in the prevention of acne has been described in patent application KR 2001931, in compositions further comprising exfoliants selected from plant proteases such as papain and bromelain, or arising from microorganisms.

An anti-acne composition of traditional Chinese medicine has been described in application CN 11040971: it comprises 10 parts *Acorus calamus* called "shi chang pu," eight parts *Schisandra* fruit, and three other plants.

DESCRIPTION OF THE INVENTION

The Inventors have discovered that *Schisandra sphenanthera* fruit extracts have cosmetic and dermatological properties that have never been described before now. In particular, it is the first time that *Schisandra sphenanthera* extracts have been used for their specific properties and not as an alternative to *Schisandra chinensis*.

The object of the invention is a cosmetic, dermatological or nutraceutical composition comprising a *Schisandra sphenanthera* fruit extract, optionally in combination with a suitable excipient.

Several *Schisandra sphenanthera* fruit extracts may be obtained and used, alone or in combination.

The *Schisandra sphenanthera* fruit extract is selected from at least:
one peptide and sugar extract;
one crude oil with the analytical results indicated in following table 3:

TABLE 3

Analytical results of crude *Schisandra sphenanthera* oil

| Oil fraction | % |
| --- | --- |
| C14 | 0 |
| C16 | 7.7 |
| C16' | 0.4 |
| C18 | 2.4 |
| C18' | 13.3 |
| C18" | 75.0 |
| C18''' | 0.5 |
| C20 | 0.5 |
| C20' | 0.2 |
| C22 | 0 |
| C22' | 0 |
| C24 | 0 |
| Tocopherol content (g/100 g) | 0.01 |
| Sterol content (g/100 g) | 0.54 |
| Lignan content (g/100 g) | 6.2 |
| Terpene content (g/100 g) | 21.4 | one refined oil with the characteristics presented in table 4, and in particular having no or very little (insignificant quantities of) terpenes:

TABLE 4

Analytical results of a refined *Schisandra sphenanthera* oil

| Oil fraction | % |
| --- | --- |
| C14 | 0 |
| C16 | 7.5 |
| C16' | 0.1 |
| C18 | 2.4 |
| C18' | 13.3 |
| C18" | 75.5 |
| C18''' | 0.5 |
| C20 | 0.5 |
| C20' | 0.2 |
| C22 | 0 |
| C22' | 0 |
| C24 | 0 |
| Tocopherol content (g/100 g) | 0.01 |
| Sterol content (g/100 g) | 0.74 |
| Lignan content (g/100 g) | 7.8 | one concentrate of said refined oil, or
one unsaponifiable arising from said refined oil concentrate.

According to a first variant of the invention, the *Schisandra sphenanthera* fruit extract is a peptide and sugar extract, comprising no lignans.

The term "peptide extract" refers to an extract comprised primarily of peptides.

The term "sugar extract" refers to an extract comprised primarily of monosaccharides.

The peptide extract according to the invention advantageously has the following specifications:

| | |
|---|---|
| Peptide content (%) | 5-90 |
| Total sugar content (%) | 5-90 |

According to a preferred aspect of the invention, the peptide and sugar extract consists of 10% to 50% by weight of peptides and from 10% to 60% by weight of sugar, wherein the percentages are expressed in relation to the total weight of said extract.

According to a second variant of the invention, the *Schisandra sphenanthera* fruit extract is a lipid extract selected from a crude oil, a refined oil, a concentrate of said refined oil or an unsaponifiable arising from said concentrate.

The lipid extracts (crude oil, refined oil) may be obtained by several methods:
- physical extraction such as cold pressing on a mechanical press, pressing on a twin-screw extruder, etc.;
- chemical extraction using organic solvents (aliphatic alkanes, alcohols, chlorinated solvents, fluorinated solvents, etc.);
- extraction in a supercritical medium, using carbon dioxide alone and/or with cosolvents.

It will be preferred, for the extraction of *Schisandra sphenanthera* oil, to use a solvent in a supercritical medium such as carbon dioxide.

Crude *Schisandra sphenanthera* oil is refined according to a molecular distillation method in order to eliminate the terpene fraction. The refined oil is thus a "terpene-free crude oil."

The term "concentrate" refers to a refined oil having undergone a molecular distillation step.

The term "unsaponifiable" refers to the unsaponifiable fraction of the refined oil concentrate, obtained after a saponification step and a step of extraction of the unsaponifiable using a suitable solvent.

Thus, the invention also relates to a method for the preparation of a refined *Schisandra sphenanthera* oil from a crude oil according to the invention, comprising a step of molecular distillation of said crude oil.

Said molecular distillation step is preferably carried out using a device selected from centrifugal molecular distillers and wiped-film molecular devices.

Centrifugal molecular distillers are known to the person skilled in the art. For example, application EP 493 144 describes a molecular distiller of this type. Generally, the product to be distilled is spread out in a thin layer over the heated surface (hot surface) of a conical rotor turning at high speed. The distillation chamber is placed under vacuum. Under these conditions, there is evaporation and not boiling from the hot surface of the constituents of the oil, such as terpenes, the advantage being that the oil and its constituents, notably the unsaponifiables (these products being considered fragile), are not degraded during the process.

Wiped-film molecular distillers, also known to the person skilled in the art, comprise a distillation chamber equipped with a rotating wiper blade, enabling continuous spreading on the evaporation surface (hot surface) of the products to be distilled. The vapors of the product are condensed by means of a cold finger placed at the center of the distillation chamber. The peripheral supply and vacuum systems are very similar to those of a centrifugal distiller (supply pumps, rotary vane vacuum pumps, oil diffusion pumps, etc.). The residues and distillates are recovered by gravitational flow.

The invention also relates to a method for the preparation of a refined *Schisandra sphenanthera* fruit oil concentrate, concentrated in its unsaponifiable fraction. This method comprises a step of molecular distillation of a refined oil. In particular, the molecular distillation step is carried out using a device selected from the centrifugal molecular distillers and wiped-film molecular devices described above.

The invention also relates to a method for the preparation of a *Schisandra sphenanthera* fruit unsaponifiable, comprising a step of saponification of a refined *Schisandra sphenanthera* fruit oil concentrate according to the invention, and then extraction of said unsaponifiable using a suitable solvent. Said extract is then washed until the soaps are completely eliminated and then the solvent is evaporated. Finally, the unsaponifiable undergoes steam deodorization followed by nitrogen stripping in order to eliminate traces of solvent and water.

The invention also has as an object a method for the preparation of a *Schisandra sphenanthera* fruit peptide and sugar extract. Said method for the preparation of a *Schisandra sphenanthera* fruit peptide and sugar extract comprises the following successive steps:
a) from *Schisandra* fruit, extraction of a crude oil and an oil cake and recovery of said oil cake which is dispersed in water;
b) enzymatic treatment of said oil cake by an enzymatic mixture of cellulases, proteases, and alpha-amylases, then;
c) heat treatment in order to inhibit the enzymes;
d) centrifugation, ultrafiltration and diafiltration on a membrane having a 15 kDa cutoff in order to eliminate residual proteins;
e) nanofiltration in order to eliminate mineral salts or free amino acids, for example;
f) the peptide extract may be bleached in the presence of activated carbon and then it is recovered after filtration.

Advantageously, the peptide and sugar extract may be freeze-dried.

According to one aspect of the invention, the cosmetic, dermatological or nutraceutical composition comprises at least two *Schisandra sphenanthera* fruit extracts. In particular, the composition comprises a peptide and sugar extract and a crude oil, or a peptide and sugar extract and a refined oil, or a peptide and sugar extract and a refined oil concentrate, or a peptide and sugar extract and an unsaponifiable.

According to another aspect of the invention, the cosmetic, dermatological or nutraceutical composition may further comprise at least one other active compound in addition to the *Schisandra sphenanthera* fruit extract.

Said other compound may be selected from all the compounds and the functional equivalents thereof mentioned below.

Said other compound may be in particular selected from the active agents typically used in dermatology such as emollients, moisturizing active agents, keratin synthesis activators, keratoregulating agents, keratolytics, agents that restructure the cutaneous barrier (activators of cutaneous lipid synthesis), peroxisome proliferator-activated receptor (PPAR) agonists, RXR or LXR agonists, vitamin D or corticosteroid receptor agonists, keratinocyte differentiation activators (retinoids, Calcidone®, calcium), sebum-regulating agents, anti-irritant agents, soothing agents, anti-inflammatory agents, antioxidants and anti-aging agents.

Said other compound may also be selected from active agents having a complementary therapeutic action, such as antibiotics, prebiotics and probiotics, anti-bacterial agents, antifungal compounds, antiviral agents, preservatives, immunomodulators (tacrolimus or pimecrolimus), oxazolines, growth factors, cicatrizing agents or eutrophic molecules, pigmenting or hypopigmenting agents, lipolytic agents or lipogenesis inhibitors or anti-cellulite or reducing agents, inorganic or organic sun filters and screens (pigmentary or ultrafine), traditional or functional foods: hyperglycemic or hypoglycemic, anti-fat or anti-cellulite nutrients, anti-cholesterol, antioxidant, energizing, reconstituting, having an impact on the secondary signs of menopause.

Said other compound may also be selected from natural plant extracts (from plants that can be extracted in an aqueous or oil phase: polyphenols, flavonoids, other peptides and sugars, etc.), compounds containing vegetable oil unsaponifiables, sterol unsaponifiables or products containing same (vegetable oil unsaponifiables, notably soya oil unsaponifiables, vegetable butter unsaponifiables or butyraceous matter and mixtures thereof, natural wax unsaponifiables, oil extract unsaponifiables, unsaponifiables of oil industry by-products, animal-fat extract unsaponifiables, marine animal oil unsaponifiables, milk-fat extract unsaponifiables, lipid unsaponifiables extracted from unicellular organisms, lipid unsaponifiables extracted from algae and marine organisms, etc.), sterols, stanols, phytosterols, phytostanols, tocopherols, sunflower and/or rapeseed and/or palm oil concentrates, trace elements, vitamins, omega-3 or -6 or -9 fatty acids, hypoglycemic or hyperglycemic or sweetening plants.

The most commonly used moisturizing/emollient active agents are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, polyunsaturated and monounsaturated omega-3, -6, -7 and -9 fatty acids such as linoleic acid and palmitoleic acid, sunflower oleodistillate, avocado peptides, cupuacu butter.

The keratin synthesis activators that may be used in combination are advantageously retinoids, lupin peptides, key proteins of the stratum corneum or granulosum (keratins) and corneodesmosomes, avocado sugars, quinoa peptide extract.

Anti-inflammatory/anti-irritant and soothing agents limit the inflammatory reaction caused by cytokines or arachidonic acid metabolism mediators and have soothing and anti-irritant properties. The most traditional are glycyrrhetinic acid (licorice derivatives) and salts and esters thereof, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide® (oxazoline derivative), isoflavones such as, for example, genistein/genistin, daidzein/daidzin, spring water or thermal spring water (eau d'Avène, eau de la Roche Posay, eau de Saint Gervais, eau d'Uriage, eau de Gamarde), goji extracts (*Lycium barbarum*), plant amino acid peptides or complexes, topical dapsone, or steroidal anti-inflammatory drugs (SAIDs) such as corticosteroids or non-steroidal anti-inflammatory drugs (NSAIDs).

The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®), the combination of glycolic acid or lactic acid with arginine or the combination of hydroxy acid with lipid molecules such as LHA® (lipo-hydroxy acid), amphoteric hydroxy acid complexes (AHCare), willow bark (*Salix alba* bark extract), azelaic acid and salts and esters thereof, salicylic acid and derivatives thereof such as capryloyl salicylic acid or in combination with other molecules such as the combination of salicylic acid and polysaccharide (beta-hydroxy acid, or BHA), tazarotene, adapalene, as well as molecules of the retinoid family such as tretinoin, retinaldehyde, isotretinoin and retinol.

The sebum-regulating agents that may be used in combination are advantageously selected from the group comprising 5-α-reductase inhibitors such as, for example, the active agent 5-αAvocuta®. Zinc (and gluconate salts thereof, salicylate and pyroglutamic acid) also has se-suppressing activity. Mention may also be made of spironolactone, an antiandrogen and aldosterone antagonist, which significantly reduces the sebum secretion rate after 12 weeks of application. Other molecules such as, for example, *Cucurbita pepo*, extracted from pumpkin seeds, squash seed oil and palm cabbage limit sebum production by inhibiting 5-α-reductase transcription and activity. Other sebum-regulating agents of lipid origin that act on sebum quality, such as linoleic acid, are of interest.

The growth factors that may be used in combination are advantageously becaplermin and transforming growth factor beta (TGF-β), EGF, NGF and VEGF.

The term "antioxidant" refers to a molecule that decreases or prevents the oxidation of other chemical substances. The antioxidants that may be used in combination are advantageously selected from the group comprised of thiols and phenols, licorice derivatives such as glycyrrhetinic acid and salts and esters thereof, alpha-bisabolol, *Ginkgo biloba* extract, *Calendula* extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the large family of polyphenols such as tannins, phenolic acids, anthocyanins, flavonoids such as, for example, extracts of green tea, of red berries, of cocoa, of grapes, of *Passiflora incarnata* or of *Citrus*, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function and stimulate the synthesis of the key lipids of the epidermis which may be used in combination are advantageously vitamin A, panthenol (vitamin B5), avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (*Acacia catechu*).

The trace elements that may be used are advantageously selected from the group comprised of copper, magnesium, manganese, chromium, selenium, silicon, zinc and mixtures thereof. Sunflower concentrates, more advantageously linoleic sunflower concentrates may also be used, such as the active agent sold by Laboratoires Expanscience, Soline®, vegetable oil unsaponifiables, such as Avocadofurane®, PPAR agonists (rosiglitazone, pioglitazone), RXR and LXR.

The anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The antifungal compounds that may be used in combination are advantageously econazole and ketoconazole.

The antiseptic preservatives that may be used in combination are, for example, triclosan, chlorhexidine and quaternary ammonium.

The antibiotics that may be used in combination are advantageously fusidic acid, penicillin, tetracyclines, pristinamycin, erythromycin, clindamycin, mupirocin, minocycline and doxycycline. The antiviral agents that may be used in combination are advantageously acyclovir and valacyclovir.

The preservatives that may be used in combination are, for example, those generally used in cosmetics or nutraceuticals, molecules with anti-bacterial activity (pseudo-preservatives) such as caprylic derivatives like, for example, capryloyl glycine and glyceryl caprylate, such as hexanediol and sodium levulinate, zinc and copper derivatives (gluconate and PCA), phytosphingosine and derivatives thereof, benzoyl peroxide, piroctone olamine, zinc pyrithione and selenium sulfide.

The sun protection active agents that may be used in combination include UVB and/or UVA sun filters or screens, or any inorganic and/or organic screens or filters known to the person skilled in the art, who will adapt their choice and their concentrations according to the degree of protection sought.

As examples of sun protection active agents, particular mention may be made of titanium dioxide, zinc oxide, methylene bis-benzotriazolyl tetramethylbutylphenol (brand name: Tinosorb M) and bis-ethylhexyloxyphenol methoxyphenyl triazone (brand name: Tinosorb S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA and diethylhexyl butamido triazone.

The reducing agents that may be used in combination are advantageously caffeine, wrack, plant extracts (such as, for example: ivy, cocoa, guarana, butcher's-broom (*Ruscus*), green tea, matè, Sichuan pepper and horse chestnut extracts), *Centella asiatica*, carnitine, glaucine, escin, isoflavones such as, for example, genistein and *Ginkgo biloba*, forskolin, retinol and other retinoids, phlorizin and sea fennel.

The agents that prevent hair loss and/or strengthen the hair and nails are advantageously phytosterols, isoflavones such as, for example, soya isoflavones, RTH16®, Aminexil®, Minoxidil®, retinol, zinc and derivatives thereof, neoruscine, vitamin E, vitamin B2, vitamin B3, vitamin B6, vitamin PP, vitamin B5 (panthenol, bepanthen), vitamin B8 (vitamin H or biotin), vitamin B9 (folic acid), alpha hydroxy acid, quinine and certain amino acids such as cysteine, cystine and methionone. Other compounds that may be used include 5-α-reductase inhibitors such as, for example, finasteride, dutasteride, *Serenoa serrulata* or repens, *Cucurbita pepo* extract or certain phytosterols. Mention may also be made of keratin, trace elements, mineral salts, certain plant protein or lipid extracts such as, for example, *Pfaffia*, sage, lemon, ginseng, quinquina, jojoba, horse chestnut, honey, wheat, nettle, echinea or coconut extracts.

The anti-dandruff agents (for the scalp) are advantageously selected from *Nasturtium* extract, vitamin F, thymol, clay, zinc pyrithione, zinc-PCA, zinc gluconate, zinc sulfate, camphor, myrtle extract, salicylic acid, vitamin B5, climbazole, ichthyol, selenium and derivatives thereof, squash seed extract, *Carthamus* extract, *Melaleuca* oil extract, borage and *Mimosa tenuiflora* oil, propolis, kertyol, glycolic acid, keluamid, cyclopiroxolamine, piroctone olamine, capryloyl glycine and 5-α Avocuta.

The drugs or cosmetic agents that may be used in combination are advantageously the drugs suitable for the prevention and/or the treatment of:
  atopy: corticosteroids such as hydrocortisone, desonide, fluocinolone acetonide, fluticasone propionate, calcineurin-inhibiting topical immunomodulators such as tacrolimus and pimecrolimus, cyclosporine, azathioprine, methotrexate, vitamin B12, antimicrobial molecules, antihistamines such as hydroxyzine and diphenhydramine, antibiotics, probiotics, naltrexone, PPAR-α agonists such as sunflower oleodistillate, emollients containing ceramides or other key epidermal lipids,
  acne: antibiotics, benzoyl peroxide, retinoids, azelaic acid, vitamin PP, vitamin B3, zinc, cyclins,
  eczema: immunomodulators, emollients, salmon oil, borage oil, probiotics,
  rosacea: permethol, genistein, esculoside, dextran sulfate, hesperidin methylchalcone, retinoids, licochalcone, oxymetazoline, kinetin, licorice extract, polyphenols, flavonoids, procyanidins (green tea), vitamin P-like, butcher's-broom extract, *Sophora japonica, Hamamelis* extract and antibiotics such as doxycycline,
  psoriasis: corticosteroids, calcipotriol, calcitriol, tazarotene, cade oil, acitretin and PUVA therapy.

The drugs or foods that may be used in combination are advantageously hyperlipidemic and/or hypolipidemic drugs or foods. Mention may be made in particular of sulfonylurea-based and glinide-based drugs, alpha-glucosidase inhibitor-based drugs, biguanide-based drugs (metformin), drugs containing insulin sensitivity activators or thiazolidinediones (TZD, pioglitazone, rosiglitazone), which are PPAR agonists, hypolipidemic drugs of the statin family or the fibrate family (PPAR-α agonists), orlistat (Xenical) and sibutramine (Reductyl or Sibutral).

The anti-fat nutrients that may be used in combination are advantageously selected from the group comprised of nutrients that block the absorption of fats, such as chitosan, nutrients capable of increasing thermogenesis (fat burners) such as ephedrine (Chinese herb *ma huang*), caffeine, theophylline and theobromine and *Citrus aurantium*, nutrients capable of controlling the appetite (hunger suppressors) such as L-phenylalanine and L-tyrosine, nutrients capable of controlling glycemia such as minerals, for example chromium or vanadium or magnesium, or the ayurvedic herb *Gymnema sylvestre*, lipogenesis inhibitors such as *Garcinia cambogia* hydroxycitric acid extract and nutrients capable of transporting fats such as L-carnitine.

Examples of hyperglycemic foods or therapies to re-equilibrate glycemia include anti-retroviruses, glucocorticoids, immunosuppressors, IFN-α, sex steroids, THS, the pill, growth hormones, sympathomimetics, cardiovascular drugs, diuretics, beta-blockers, calcium inhibitors and psychotropics.

The hypoglycemic plants that may be used in combination are advantageously selected from the group comprised of fenugreek (*Trigonella foenum-graecum*), corosolic acid (active compound of the leaves of the *Lagerstroemia speciosa* tree), *Gymnema sylvestre, Momordica charantia* fruit juice, eucalyptus (*Eucalyptus globulus*), *Panax ginseng* and whortleberry (*Vaccinium myrtillus*) leaves.

The immunomodulators that may be used in combination are advantageously tacrolimus, pimecrolimus and oxazolines. The oxazolines that may be used in combination are advantageously oxazolines selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. Even more advantageously, said oxazoline is 2-undecyl-4,4-dimethyl-1,3-oxazoline, called OX-100 or Cycloceramide®.

The hypopigmenting or depigmenting agents that may be used in combination include hydroquinone and derivatives thereof, arbutin, retinoic acid, retinol, retinaldehyde, tretinoin, hydroquinone, corticosteroids, kojic acid, azelaic acid, ellagic acid, pyruvic acid, glycolic acid, vitamin B3 (niacinamide) or PP, vitamin C, Cycloceramide®, resorcinol derivatives, resveratrol, licorice or white mulberry extracts, alpha-lipoic acid, linoleic acid, indomethacin, cation chelators such as ethylenediaminetetraacetic acid (EDTA), and soya extracts such as genistein. Mention may also be made of Sepiwhite® (N-undecylenoyl-L-phenylalanine) sold by Seppic, which is a cosmetic depigmenting agent.

The pigmenting agents that may be used in combination are, for example, agents that color the skin such as dihydroxyacetone and melanins; agents that stimulate the natural pigmentation process such as psoralens having therapeutic properties in dermatology (8-methoxypsoralen, 5-methoxypsoralen, 4,5',8-trimethylpsoralen or plant extracts of *Psoralea corylifolia* and *Ammi majus*), carotenoids (lycopene, canthaxanthin), agents that stimulate the cyclic AMP pathway (1. cAMP analogues, such as 8-bromo-cAMP or dibutyryl-cAMP, 2. forskolin, 3. isobutyl-methylxanthine or theophylline), protein kinase C activators (diacylglycerols, in particular oleyl-acetyl-glycerol), aliphatic or cyclic diols (1,2-propanediol, 5-norbornane-2,2-dimethanol, norbornane-2,2-dimethanol), bicyclic monoterpene diols, tyrosine derivatives (L-tyrosine, L-DOPA), dimethylsulfoxide, lysosomotropic agents, thymidine dinucleotides, DNA fragments, melanocyte stimulating hormone analogs, 3-isobutyl-1-methylxanthine, nitric acid donors (Brown, Journal of photochemistry and photobiology B: biology 63 (2001) 148-161); or plant extracts such as rice peptides, and algae that show pro-melanogenesis activity: *Laminaria digitata* (Thalitan® from Codif).

A particularly advantageous combination according to the invention is a composition comprising the *Schisandra sphenanthera* fruit peptide and sugar extract and plant and animal unsaponifiables such as, for example, avocado and soya unsaponifiables, and unsaponifiable plant or animal oil concentrates such as, for example, sunflower or palm oil concentrates, or plant oils containing unsaponifiables such as, for example, soya and rapeseed oils, and derivatives of unsaponifiables such as avocado furans, sterol esters and vitamin derivatives. "Sterol" unsaponifiables are unsaponifiables whose content of sterols, methylsterols and triterpene alcohols range from 20% to 95% by weight, preferably 45% to 65% by weight, in relation to the total weight of the unsaponifiable.

A particularly advantageous combination according to the invention is a composition comprising the *Schisandra sphenanthera* fruit extract and avocado sugars (such as described in application WO 2005/115421). Said composition is particularly suited for the treatment of cutaneous barrier repair and inflammation.

A particularly advantageous combination according to the invention is a composition comprising the *Schisandra sphenanthera* fruit extract and avocado peptides (such as described in international application WO 2005/105123). Said composition is particularly suited for the treatment of irritation and inflammation.

Another particularly advantageous combination according to the invention is a composition comprising the *Schisandra sphenanthera* fruit extract and avocado oil (such as described in international applications WO 2004/012496, WO 2004/012752, WO 2004/016106, WO 2007/057439).

Another particularly advantageous combination according to the invention is a composition comprising the *Schisandra sphenanthera* fruit extract and Avocadofurane® (avocado furans, which may be obtained by the method described in international application WO 01/21605). Said composition is particularly suited for the treatment of inflammation, to promote cicatrization, and for its anti-aging properties.

Another particularly advantageous combination according to the invention is a composition comprising the *Schisandra sphenanthera* fruit extract and 5-αAvocuta® (butyl avocadate). Said composition is particularly suited for inhibiting 5-α-reductase (see WO 01/52837 and WO 02/06205) and for regulating the increased seborrheic secretion found in acne and dandruff.

Another particularly advantageous combination according to the invention is a composition comprising the *Schisandra sphenanthera* fruit extract and avocado and soya unsaponifiables. The avocado and soya unsaponifiables which may be used in combination are advantageously a mixture of avocado furanic unsaponifiables and soya unsaponifiables, in a ratio of roughly 1:3-2:3, respectively. The avocado and soya unsaponifiables are even more advantageously the product Piascledine®, sold by Laboratoires Expanscience.

Another particularly advantageous combination according to the invention is a composition comprising the *Schisandra sphenanthera* fruit extract and a sunflower oleodistillate, even more advantageously with linoleic sunflower concentrates, such as the active agent sold by Laboratoires Expanscience, Soline® (see international application WO 01/21150). Said composition is particularly suited for the treatment of inflammation and cutaneous barrier repair.

Another particularly advantageous combination according to the invention is a composition comprising the *Schisandra sphenanthera* fruit extract and a soya unsaponifiable, such as obtained according to the method described in international application WO 01/51596.

Another particularly advantageous combination according to the invention is a composition comprising the *Schisandra sphenanthera* fruit extract and lupeol (FR 2 822 821, FR 2 857 596). Said composition is particularly suited to support cicatrization.

Another particularly advantageous combination according to the invention is a composition comprising the *Schisandra sphenanthera* fruit extract and lupin peptides such as obtained according to the method described in application WO 2005/102259. Said composition is particularly suited for the treatment of inflammation and is used for its anti-aging properties.

Another particularly advantageous combination according to the invention is a composition comprising the *Schisandra sphenanthera* fruit extract and a total lupin extract (see international application WO 2005/102259). Said composition is particularly suited for the treatment of irritation.

Another particularly advantageous combination according to the invention is a composition comprising the *Schisandra sphenanthera* fruit extract and lupin oil, advantageously sweet white lupin oil, such as that described in international application WO 98/47479.

Another particularly advantageous combination according to the invention is a composition comprising the *Schisandra*

*sphenanthera* fruit extract and a maca peptide extract (see international application WO 2004/112742). Said composition is particularly appreciated for its cicatrizing and anti-aging properties.

A particularly advantageous combination according to the invention is a composition comprising the *Schisandra sphenanthera* fruit peptide and sugar extract and rice peptides (see international application WO 2008/009709). Said composition is particularly appreciated for its properties related to stimulation of melanogenesis and to melanin transfer.

Another particularly advantageous combination according to the invention is a composition comprising the *Schisandra sphenanthera* fruit extract and Cycloceramide® (oxazoline derivative) such as described in international applications WO 2004/050052, WO 2004/050079 and WO 2004/112741. Said composition is particularly suited for the treatment of inflammatory reactions.

Another particularly advantageous combination according to the invention is a composition comprising the *Schisandra sphenanthera* fruit extract and a quinoa extract, in particular a peptide extract (see international application WO 2008/080974). Said composition is particularly suited for the treatment of inflammatory conditions and cutaneous barrier repair.

Another particularly advantageous combination according to the invention is a composition comprising the *Schisandra sphenanthera* fruit extract and cupuacu butter. Said composition is particularly appreciated for its moisturizing properties.

Another particularly advantageous combination according to the invention is a composition comprising the *Schisandra sphenanthera* fruit extract and rapeseed concentrate.

Another advantageous combination according to the invention is a composition comprising the *Schisandra sphenanthera* fruit extract and corn concentrate.

All these combinations comprise at least one other active compound, in addition to the *Schisandra sphenanthera* fruit extract, and may comprise two, three, four or more active compounds as described above.

The composition according to the invention may be formulated in the form of various preparations suited for topical application or for oral, rectal, vaginal, nasal, auricular, bronchial or parenteral administration.

According to a first variant, the various preparations are suited for topical application and include creams, emulsions, milks, pomades, lotions, oils, aqueous or hydro-alcoholic or glycolic solutions, powders, patches, sprays or any other product for external application.

According to a second variant, the various preparations are suited for oral administration, wherein the *Schisandra* fruit extract may be included in a dietary composition or in a dietary supplement. The dietary supplement may be provided in the form of *Schisandra sphenanthera* fruit extract as-is (refined oil, for example), or in the form of hard or soft gelatin or vegetable capsules in the context of the present invention. Said dietary supplement may thus contain from 10% to 100% by weight of the *Schisandra sphenanthera* fruit extract.

According to this second variant of the present invention, the *Schisandra sphenanthera* fruit extracts of the present invention may be incorporated, with no restriction, in foods, beverages and nutraceuticals, including the following:

1) Dairy products such as cheese, butter, milk and other lacteal beverages, mixtures and spreads containing lacteal products, ice cream and yogurt;
2) Fat-based products such as margarine, spreads, mayonnaise, cooking fats, frying oils and vinaigrettes;
3) Cereal-based products composed of grains such as bread and pasta, whether these food products are cooked, baked or processed.
4) Confections such as chocolate, candy, chewing gum, desserts, toppings, sorbets, icing and other garnishes;
5) Alcoholic or non-alcoholic beverages including sodas and other soft drinks, fruit juices, diet supplements, meal replacements in beverage form such as those sold under the brand names Boost™ and Ensure™, and;
6) Various products such as eggs, processed food such as soup, ready-to-use pasta sauces, prepared dishes and other products of the same type.

The composition of the present invention may be incorporated directly and with no other modification in foods, in nutraceuticals, in diet products, in particular high-protein products, or in beverages by virtue of techniques such as mixing, infusion, injection, blending, absorption, kneading and spraying.

The modes of administration, dosing schedules and optimal galenic forms of the compounds and compositions according to the invention may be determined according to criteria generally taken into account in the establishment of a pharmaceutical treatment, in particular a dermatological treatment, or a veterinary treatment suited to a patient or to an animal such as, for example, the patient's or animal's age or weight, the gravity of the patient's or animal's general state, tolerance to the treatment, noted side effects and skin type. According to the type of administration desired, the active composition and/or compounds according to the invention may further comprise at least one pharmaceutically acceptable excipient, in particular dermatologically acceptable. According to the first variant, an excipient suited for external topical application is used. The composition according to the present invention may further comprise at least one pharmaceutical adjuvant known to the person skilled in the art, selected from thickeners, preservatives, fragrances, colorants, chemical or mineral filters, moisturizing agents, thermal spring water, etc.

The composition comprising a *Schisandra sphenanthera* fruit extract having the specifications indicated is particularly intended for a cosmetic, dermatological or nutraceutical use.

In the context of a cosmetic or dermatological use, the composition will advantageously be formulated in the form of a preparation suited for topical application. The composition comprising a peptide and sugar extract is particularly intended for a cosmetic or dermatological use.

In the context of a nutraceutical use, to nutritive or cosmetic ends (cosmetic foods), the composition will advantageously be formulated in the form of a preparation suited for oral administration. It will not comprise an excipient and will be comprised, in whole, of refined *Schisandra sphenanthera* oil.

The invention also has as an object the use of a *Schisandra sphenanthera* fruit extract, selected from a *Schisandra sphenanthera* fruit peptide and sugar extract or a *Schisandra sphenanthera* fruit lipid extract, wherein said *Schisandra sphenanthera* fruit lipid extract is selected from the group comprised of a crude oil, a refined oil, a concentrate or an unsaponifiable, for the manufacture of a cosmetic or dermatological or food composition.

In a first aspect, the invention has as an object the use of a *Schisandra sphenanthera* fruit extract, selected from a peptide and sugar extract or a crude oil or a refined oil or a concentrate or an unsaponifiable such as defined above, for the prevention and treatment of allergic, inflammatory or irritative reactions or pathologies, or of disorders of the barrier or the homeostasis of the skin and/or the mucosa and/or of immature, normal or mature/aged epithelial appendages, in a cosmetic composition.

In a second aspect, the invention has as an object the use of a *Schisandra sphenanthera* fruit extract, selected from a peptide and sugar extract or a crude oil or a refined oil or a concentrate or an unsaponifiable such as defined above, for the prevention and treatment of allergic, inflammatory or irritative reactions or pathologies, or of disorders of the barrier or the homeostasis of the skin and/or the mucosa and/or of immature, normal or mature/aged epithelial appendages, in a food composition such as a functional food.

A functional food is a conventional food, or which appears to be a conventional food, which is part of a normal diet, and which has as a characteristic to provide beneficial physiological effects that exceed its typical nutritional functions or to reduce the risk of chronic diseases.

In particular, the functional food is intended for the prevention and treatment of allergic, inflammatory or irritative reactions or pathologies or of disorders of the barrier or of homeostasis of the:

skin, such as acne, rosacea (erythro-couperose), cutaneous redness, psoriasis, vascular disorders, diaper rash, atopic dermatitis, eczema, contact dermatitis, irritative dermatitis, allergic dermatitis, seborrheic dermatitis (cradle cap), psoriasis, sensitive skin, reactive skin, dry skin (xerosis), dehydrated skin, skin with redness, cutaneous erythema, aged and photo-aged skin, photo-sensitive skin, pigmented skin (melasma, post-inflammatory pigmentation, etc.), depigmented skin (vitiligo), skin with cellulitis, loose skin, skin with stretch marks, scurf, chapping, insect bites, cracks in particular of the breasts, sunburn, inflammations due to rays of all kinds, irritations by chemical agents, physical agents (tension stress: pregnant women), bacteriological agents, fungal or viral agents, parasitic agents (lice, mites, ringworm, acarina, dermatophytes) or radiological agents or by innate immunity deficits (antimicrobial peptides) or acquired immunity deficits (cellular, humoral, cytokines), and/or mucosa, such as gums and periodontium with gingivitis (sensitive gums in newborns, hygiene problems due to tobacco use, etc.), periodontal disease, or genital mucosa with irritations of the internal or external male or female genital regions, and/or epithelial appendages such as immature, normal or mature nails (breakable, fragile nails, etc.) and hair (alopecia, dandruff, hirsutism, seborrheic dermatitis, folliculitis), exhibiting in particular scalp disorders such as androgenetic, acute, localized, cicatricial or congenital alopecia, occipital alopecia in newborns, alopecia aerata, alopecia due to chemotherapy/radiotherapy or telogen effluvium, anagen effluvium, pilar dystrophy, trichotillomania, tinea or oily or dry dandruff.

The invention also relates to a food or a nutraceutical composition comprising a *Schisandra sphenanthera* fruit extract, selected from a *Schisandra sphenanthera* fruit peptide and sugar extract or *Schisandra sphenanthera* fruit lipid extract, wherein said lipid extract is itself selected from the group comprised of a crude oil, a refined oil, a concentrate or an unsaponifiable.

In a third aspect, the invention has as an object the therapeutic use of a *Schisandra sphenanthera* fruit extract, selected from a peptide and sugar extract or a crude oil or a refined oil or a concentrate or an unsaponifiable such as defined above, for the prevention and treatment of allergic, inflammatory or irritative reactions or pathologies, or of disorders of the barrier or the homeostasis of the skin and/or the mucosa and/or of immature, normal or mature/aged epithelial appendages.

According to a preferred aspect, the invention has as an object the use of a *Schisandra sphenanthera* fruit peptide and sugar extract for the treatment and prevention of cutaneous redness, erythro-couperose and rosacea in a cosmetic composition.

According to another preferred aspect, the invention has as an object the use of a *Schisandra sphenanthera* fruit peptide and sugar extract for the treatment and prevention of cutaneous redness, erythro-couperose and rosacea in a food composition.

According to a third preferred aspect, the invention has as an object the therapeutic use of a *Schisandra sphenanthera* fruit peptide and sugar extract for the treatment and prevention of cutaneous redness, erythro-couperose and/or rosacea.

EXAMPLES

Example 1

Compositions for Topical Application

The Inventors present below several compositions for topical application. The oil, the refined oil concentrated in lignans, the unsaponifiable fraction and the *Schisandra sphenanthera* peptide and sugar extract may be incorporated in various cosmetic products such as cleansing water, oil-in-water emulsions, water-in-oil emulsions, oils, milks, lotions, shampoos, foaming products and sprays, whose compositions are presented below.

| Raw material/brand name | % |
|---|---|
| Moisturizing cleansing water | |
| Purified water | QSP 100% |
| Biosaccharide gum | 1%-5% |
| Butylene glycol | 1%-5% |
| Hyaluronic acid | 0%-5% |
| *Schisandra* peptide and sugar extract | 0.01%-5% |
| Preservatives | 0%-1% |
| Citric acid monohydrate | 0%-1% |
| Tromethamine | 0%-1% |
| Cleansing water for sensitive skin | |
| Capryloyl glycine | 0%-1% |
| Soda lye | 0%-1% |
| Sequestrant | 0%-1% |
| Butylene glycol | 1%-5% |
| Beta-carotene | 0%-2% |
| *Schisandra* concentrate | 0.01%-5% |
| Preservatives | 0%-1% |
| PEG-32 | 1%-5% |
| PEG-7 palmcocoate | 1%-5% |
| Zinc gluconate | 0%-1% |
| Citric acid | 0%-1% |
| Purified water | QSP 100% |
| Fragrance | 0%-1% |
| Poloxamer 184 | 1%-5% |
| Anti-aging emulsion | |
| Liquid isoparaffin | 5%-20% |
| Isocetyl stearate | 5%-20% |
| Al—Mg hydroxystearate | 5%-20% |
| Abil WE 09 | 1%-5% |
| Glycerol | 1%-5% |
| Vaseline oil | 1%-5% |
| Micronized zinc oxide | 1%-5% |
| Butylene glycol | 1%-5% |
| Retinol | 0%-1% |

| Raw material/brand name | % |
|---|---|
| Vitamin C | 0%-5% |
| *Schisandra* unsaponifiable fraction | 0.01%-5% |
| Isononyl isononanoate | 1%-5% |
| Beeswax | 1%-5% |
| Sodium tartrate | 1%-5% |
| Sodium chloride | 0%-5% |
| Glycine | 1%-5% |
| Preservatives | 0%-1% |
| Cholesterol | 0%-1% |
| Phytosphingosine | 0%-1% |
| Tartaric acid | 0%-1% |
| Purified water | QSP 100% |
| Restructuring emulsion | |
| Hydrogenated polydecene | 5%-20% |
| Lauryl-glucoside glystearate | 1%-5% |
| Dicaprylyl carbonate | 1%-5% |
| Glycerol | 5%-20% |
| Carbopol | 0%-1% |
| Xanthan gum | 0%-1% |
| Asiatic acid | 0%-1% |
| Vitamin B5 | 0%-5% |
| *Schisandra* oil | 0.01%-5% |
| Soda lye | 0%-1% |
| Preservatives | 0%-1% |
| Citric acid | 0%-1% |
| Purified water | QSP 100% |
| Reducing oil | |
| Solubilizer | 0%-1% |
| Sweet almond oil | 5%-20% |
| Copra caprylate/caprate | QSP 100% |
| Refined macadamia oil | 5%-20% |
| Glycerol caprylocaprate | 5%-20% |
| Natural alpha-bisabolol | 0%-1% |
| Alpha-tocopherol | 0%-1% |
| Ivy extract | 0%-5% |
| Refined *Schisandra* oil | 0.01%-5% |
| Preservative | 0%-1% |
| Ester | 0%-1% |
| Milk for dry, atopic skin | |
| Sweet almond oil | 1%-5% |
| Corn oil | 1%-5% |
| Stearic acid | 1%-5% |
| C16-C18 cetyl acid | 0%-1% |
| Antifoam 70414 | 0%-1% |
| Lauric alcohol 11OE | 1%-5% |
| PEG 300 monolaurate | 0%-1% |
| Glycerol monoleate | 0%-1% |
| Glycerol monostearate | 1%-5% |
| Vitamin B12 | 0%-5% |
| *Schisandra* concentrate | 0.1%-5% |
| Preservatives | 0%-1% |
| Citric acid | 0%-1% |
| Trisodium citrate | 0%-1% |
| Purified water | QSP 100% |
| Fragrance | 0%-1% |
| Peanut oil | 1%-5% |
| Hydrogenated palm oil | 1%-5% |
| Foam | |
| Purified water | QSP 100% |
| Lauroamphoacetate | 5%-20% |
| Cocoglucoside | 5%-20% |
| Surfactant 1 | 5%-20% |
| Surfactant 2 | 5%-20% |
| PEG 6000 distearate | 1%-5% |
| Preservatives | 1%-5% |
| *Schisandra* oil | 0.1%-5% |
| Chamomile extract | 1%-5% |
| Citric acid monohydrate | 0%-1% |
| Sequestrant | 0%-1% |
| Fragrance | 0%-1% |
| Soda lye | 0%-1% |

| Raw material/brand name | % |
|---|---|
| Soothing spray | |
| Purified water | QSP 100% |
| Trilaureth-4 phosphate | 1%-5% |
| Dicaprylyl carbonate | 1%-5% |
| Butylene glycol | 1%-5% |
| Erythrityl ester | 1%-5% |
| Liquid Vaseline oil | 1%-5% |
| Shea butter | 0%-1% |
| Vegetable oil | 0%-1% |
| Preservatives | 0%-1% |
| Lycopene | 0%-5% |
| *Schisandra* unsaponifiable fraction | 0.01%-5% |
| Soda lye | 0%-1% |
| Fragrance | 0%-1% |
| Xanthan gum | 0%-1% |
| Carbopol | 0%-1% |
| Sequestrant | 0%-1% |
| Citric acid | 0%-1% |
| Purifying cleansing cream | |
| Purified water | QSP 100% |
| Arlatone | 10%-30% |
| Cocoglucoside | 5%-20% |
| Hydroxypropyl guar | 1%-5% |
| Caprylyl glycine | 0%-2% |
| Preservatives | 0%-2% |
| Fragrance | 0%-1% |
| Citric acid | 0%-1% |
| Zinc PCA | 0%-1% |
| *Schisandra* peptide and sugar extract | 0.01%-5% |
| Anti-acne emulsion | |
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Vitamin E | 0%-1% |
| Vitamin B3 | 0%-5% |
| Linoleic acid | 0%-1% |
| *Schisandra* peptide and sugar extract | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |
| Anti-redness emulsion | |
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Esculoside | 0%-2% |
| Sophora japonica | 0%-5% |
| Vitamin E | 0%-1% |
| *Schisandra* oil | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |

-continued

| Raw material/brand name | % |
| --- | --- |
| Vitamin B6 | 0%-1% |
| Fragrance | 0%-1% |
| Purified water | QSP 100% |
| Reparative care | |
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Vitamin E | 0%-1% |
| Coenzyme Q10 | 0%-2% |
| Ceramide | 0%-5% |
| Refined *Schisandra* oil | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |
| Depigmenting emulsion | |
| Isononyl isononanoate | 1%-10% |
| Isocetyl stearate | 1%-10% |
| PEG 40 stearate | 1%-5% |
| PEG 5 glyceryl stearate | 1%-5% |
| Preservatives | 0%-1% |
| C16-C18 cetyl alcohol | 0%-2% |
| PPG/SMDI polymer | 0%-1% |
| Salicylic acid | 0%-2% |
| Squalane gel | 0%-2% |
| Dioctyl ether | 1%-10% |
| Dimalate alcohol | 1%-10% |
| Sunflower extract | 1%-10% |
| Tromethamine | 1%-5% |
| Butylene glycol | 1%-10% |
| Trisodium citrate | 0%-1% |
| Sclerotium gum | 0%-1% |
| Rice starch | 1%-10% |
| Polyacrylamide gel | 0%-1% |
| Vitamin C | 0%-2% |
| Glycine | 0%-2% |
| Fragrance | 0%-1% |
| Vitamin E | 0%-2% |
| Citric acid | 0%-1% |
| Sepiwhite | 0%-2% |
| *Schisandra* concentrate | 0.01%-5% |
| Purified water | QSP 100% |
| Anti-bacterial stick roll-on | |
| Purified water | QSP 100% |
| Butylene glycol | 1%-5% |
| Benzoyl peroxide | 0%-2% |
| Caprylolyl glycine | 0%-5% |
| Zinc PCA | 0%-5% |
| *Schisandra* oil | 0.1%-5% |
| Carbomer | 0%-2% |
| Preservatives | 0%-1% |
| Citric acid | 0%-1% |
| Tromethamine | 0%-1% |
| Scrub | |
| Arlatone duo | 5%-20% |
| Exfoliating agent | 1%-10% |
| Sclerotium gum | 1%-10% |
| Preservatives | 0%-1% |
| Caprylolyl glycine | 0%-1% |
| Soda | 0%-1% |
| *Schisandra* peptide and sugar extract | 0.01%-5% |
| Sequestrant | 0%-1% |

-continued

| Raw material/brand name | % |
| --- | --- |
| Citric acid | 0%-1% |
| Purified water | QSP 100% |
| Fragrance | 0%-1% |
| Keratinizing fluid | |
| Cetyl alcohol | 1%-5% |
| Silicone 345 | 1%-5% |
| Antioxidant | 0%-1% |
| Purified water | QSP 100% |
| Cetrimonium chloride | 0%-5% |
| Quinine | 0%-5% |
| Vitamin B5 | 0%-5% |
| *Schisandra* oil | 0.01%-5% |
| Hydrolyzed wheat protein | 0%-1% |
| Preservative | 0%-2% |
| Fragrance | 0%-1% |
| pH adjuster | 0%-1% |
| Antidandruff shampoo | |
| Purified water | QSP 100% |
| Lauroamphoacetate | 5%-20% |
| Cocoglucoside | 5%-20% |
| PEG 6000 distearate | 1%-5% |
| Preservatives | 0%-2% |
| Vitamin F | 0%-5% |
| Piroctone olamine | 0%-2% |
| *Schisandra* concentrate | 0.01%-5% |
| Zinc pyrithione | 0%-1% |
| pH adjuster | 0%-1% |
| Sequestrant | 0%-1% |
| Fragrance | 0%-1% |
| Conditioner | |
| Cetearyl alcohol/ceteareth-33 | 1%-5% |
| Quaternium-82 | 0%-2% |
| Purified water | QSP 100% |
| Hydrolyzed wheat protein | 0%-5% |
| Preservatives | 0%-2% |
| pH adjuster | 0%-1% |
| Fragrance | 0%-1% |
| Cysteine | 0%-5% |
| Refined *Schisandra* oil | 0.01%-5% |
| Fortifying capillary lotion | |
| Purified water | QSP 100% |
| Methyl propanediol | 5%-20% |
| Preservative | 0%-2% |
| pH adjuster | 0%-1% |
| Fragrance | 0%-1% |
| Biotin | 0%-5% |
| Vitamin B9 | 0%-5% |
| *Schisandra* concentrate | 0.01%-5% |
| Beta-sitosterol | 0%-1% |
| Ethylhexyl cocoate | 0%-5% |
| PEG-40 castor oil | 0%-5% |
| Photoprotecting stick | |
| Castor oil | QSP 100% |
| Oleic alcohol | 10%-20% |
| Palm oil | 10%-20% |
| Polyglycerin-3-beeswax | 10%-20% |
| Candelilla wax | 10%-20% |
| Hectorite | 10%-20% |
| Titanium dioxide | 0%-5% |
| *Schisandra* unsaponifiable fraction | 0.01%-5% |
| Shea butter | 0%-5% |
| Vitamin E | 0%-1% |
| SPE 50+ sun cream | |
| B4 purified water | QSP 100% |
| Titanium oxide | 10%-20% |
| Cyclopentasiloxane | 5%-15% |
| Octyl palmitate | 5%-15% |
| C12-C15 alkyl benzoate | 5%-10% |
| Decyl pentanoate | 5%-10% |
| Zinc oxide | 5%-10% |
| Glycerol | 1%-5% |
| PEG-45/dodecyl glycol copolymer | 1%-5% |

-continued

| Raw material/brand name | % |
|---|---|
| *Schisandra* peptide and sugar extract | 0.01%-5% |
| Sodium chloride | 1%-5% |
| Dextrin palmitate | 1%-2% |
| Vitamin E | 0%-2% |
| Preservatives | 0%-2% |
| Hydroxypropyl guar | 0%-1% |
| Aloe vera | 0%-1% |
| Soda lye | 0%-1% |
| EDTA 2-Na | 0%-1% |
| Zinc gluconate | 0%-1% |
| SPF 50+ sun spray | |
| Glycerol caprylocaprate | 5%-20% |
| Cyclopentasiloxane | 10%-20% |
| Dicaprylyl carbonate | 5%-20% |
| Tinosorb S | 1%-10% |
| Titanium oxide 100 | 10%-20% |
| Hectorite | 0%-5% |
| Alpha-tocopherol | 0%-2% |
| Lauryl glucoside-glystearate | 0%-10% |
| B4 purified water | QSP 100% |
| Citric acid | 0%-2% |
| Pentylene glycol | 0%-5% |
| Glycerol | 0%-5% |
| Xanthan gum | 0%-2% |
| *Schisandra* concentrate | 0.01%-5% |
| Aloe vera | 0%-1% |
| Zinc gluconate | 0%-1% |
| Preservatives | 0%-2% |
| Tinosorb M | 1%-10% |
| Anti-redness emulsion | |
| PEG 40 stearate | 1%-5% |
| PEG 5 glyceryl stearate | 1%-5% |
| Ceresin wax | 1%-5% |
| Glycerol monostearate | 1%-5% |
| Sorbitan stearate | 0%-2% |
| Cetyl alcohol | 0%-2% |
| Dimalate alcohol | 5%-20% |
| Sophora japonica | 0%-5% |
| Vitamin E | 0%-1% |
| *Schisandra* peptide and sugar extract | 0.01%-5% |
| Butylene glycol | 1%-5% |
| Piroctolamine | 0%-1% |
| Preservatives | 0%-1% |
| Glycerol | 1%-10% |
| Xanthan gum | 0%-1% |
| Zinc PCA | 0%-2% |
| Rice starch | 1%-5% |
| Nylon 6 | 0%-2% |
| Polyacrylamide gel | 1%-5% |
| Vitamin B6 | 0%-1% |
| Fragrance | 0%-1% |
| Purified water | QSP 100% |
| Anti-aging anti-redness emulsion | |
| Liquid isoparaffin | 5%-20% |
| Isocetyl stearate | 5%-20% |
| Al—Mg hydroxystearate | 5%-20% |
| Abil WE 09 | 1%-5% |
| Glycerol | 1%-5% |
| Vaseline oil | 1%-5% |
| Micronized zinc oxide | 1%-5% |
| Butylene glycol | 1%-5% |
| Retinol | 0%-1% |
| Vitamin C | 0%-5% |
| *Schisandra* peptide and sugar extract | 0.01%-5% |
| Isononyl isononanoate | 1%-5% |
| Beeswax | 1%-5% |
| Sodium tartrate | 1%-5% |
| Sodium chloride | 0%-5% |
| Glycine | 1%-5% |
| Preservatives | 0%-1% |
| Cholesterol | 0%-1% |
| Phytosphingosine | 0%-1% |
| Tartaric acid | 0%-1% |
| Purified water | QSP 100% |

Example 2

Compositions for Oral Administration

The *Schisandra* oil, concentrate and peptides are integrated into oral compositions, in compositions enabling the administration of 50 mg to 200 mg of *Schisandra* extract per day.

2.1 Anti-stretch Marks Composition in the Form of Soft Capsules

A-Composition 1

| | |
|---|---|
| *Schisandra* peptide and sugar extract | 30 mg |
| Awara oil | 60 mg |
| Unsaponifiable-rich rapeseed oil | 300 mg |
| Vitamin of group B (B1, B2, B3, B5, B6, B9, B12) | QSP 100% RDA |
| Tocotrienols | QSP 50% RDA |
| Vitamin E | |
| Beeswax | |
| Soya lecithin | |
| Alimentary gelatin | |
| Glycerin | QSP 1 soft capsule |

Said composition is administered as four to six 500 mg capsules per day.

B-Composition 2

| | |
|---|---|
| *Schisandra* oil | 30 mg |
| Cereal oil rich in ceramides and polar lipids | 300 mg |
| Lupin oil | 50 mg |
| Vitamin E | QSP 100% RDA |
| Vitamin C | QSP 50% RDA |
| Beeswax | |
| Soya lecithin | |
| Alimentary gelatin | |
| Glycerin | QSP 1 soft capsule |

Said composition is administered as four to six 500 mg capsules per day.

2.2 Anti-hair Loss Tablets

| | |
|---|---|
| *Schisandra* concentrate | 25 mg |
| Cereal extracts (corn, buckwheat, millet, spelt) rich in sulfur amino acids | 200 mg |
| Vitamin C | QSP 50% RDA |
| Fish cartilage glycosaminoglycans | 200 mg |
| Glucidex IT 19 (compression agent) | QSP one 800 mg tablet |

Said composition is administered as five to eight tablets per day.

| | |
|---|---|
| *Schisandra* unsaponifiable fraction | 200 mg |
| Cereal extracts (corn, buckwheat, millet, spelt) rich in sulfur amino acids | 200 mg |
| Zn in chelate form | QSP 100% RDA |
| Vitamin C | QSP 50% RDA |
| Fish cartilage glycosaminoglycans | 200 mg |
| Fruit flavor (citrus fruits, red berries), potassium acesulfame, Glucidex IT 19 (compression agent) | QSP one 2000 mg tablet |

Said composition is administered once per day.

2.3 Examples of Reducing Powder Sticks

| | |
|---|---|
| *Schisandra* peptide and sugar extract | 100 mg |
| Polyphenol-rich tea extract | 100 mg |
| OPC-rich grape extract | 50 mg |
| Plant beta-glucans | 100 mg |
| Xanthan gum | 1 mg |
| Sodium ascorbate | 0.3 mg |
| Maltodextrin | QSP 5 g |

Said composition is administered twice per day.

| | |
|---|---|
| *Schisandra* unsaponifiable fraction | 100 mg |
| Centella asiatica extract | 100 mg |
| Magnesium, selenium, manganese | QSP 100% RDA |
| Xanthan gum | 1 mg |
| Sodium ascorbate | 0.3 mg |
| Maltodextrin | QSP 5 g |

Said composition is administered twice per day.

2.4 Example of a Chocolate-flavored Cereal Bar

| | |
|---|---|
| Refined *Schisandra* oil | 200 mg |
| Lycopene | 6 mg |
| Astaxanthin | 4 mg |
| Fucoxanthin | 4 mg |
| Lutein in microencapsulated form | 4 mg |
| Microencapsulated tocotrienol | QSP 100% RDA in vitamin E |
| Black Chocolate, oligofructose, sugar, fructose syrup, fat-reduced cocoa, crunchy cereals, powdered skim milk, almonds, glycerol, sorbitol, vegetable oils, glucose syrup, flavoring, sweetened condensed milk, soya lecithin, fatty acid mono- and diglycerides, caramelized syrup, maltodextrin, salt, potassium sorbate, alpha-tocopherol | QSP one 50 g bar |

Said composition is administered once per day.

2.5 Example of a Vanilla-flavored Cereal Bar

| | |
|---|---|
| *Schisandra* oil | 200 mg |
| Cereal extracts (corn, buckwheat, millet, spelt) rich in sulfur amino acids | 200 mg |
| Fish cartilage glycosaminoglycans | 200 mg |
| Polyphenol-rich green tea extract | 200 mg |
| Oligofructose, sugar, fructose syrup, crunchy cereals, powdered skim milk, almonds, glycerol, sorbitol, vegetable oils, glucose syrup, flavoring, sweetened condensed milk, soya lecithin, fatty acid mono- and diglycerides, caramelized syrup, maltodextrin, salt, potassium sorbate, alpha-tocopherol | QSP one 50 g bar |

Said composition is administered once per day.

2.6 Example of a Praline-flavored Lacteal Beverage

| | |
|---|---|
| *Schisandra* concentrate | 200 mg |
| Polyphenol-rich green tea extract | 100 mg |
| Vitamin of group B (B1, B2, B3, B5, B6, B9, B12) | QSP 100% RDA |
| Zn, Mg, Se | QSP 100% RDA |
| Skimmed milk powder, flavoring, fructose, egg white, hazel nuts, sugar, caramel, beta-carotene, xanthan gum, aspartame, potassium acesulfame, soya lecithin, maltodextrin | QSP one 30 g packet |

Said composition is administered once per day.

Example 3

Activity of a *Schisandra Sphenanthera* Peptide and Sugar Extract in the Inflammatory Phase of Rosacea In examples 3 to 5, the expression "*Schisandra* peptides" refers to the *Schisandra sphenanthera* peptide and sugar extract containing a certain percentage of peptides.

In order to evaluate the potential activity of *Schisandra* peptides in the inflammatory phase of rosacea, we studied the effect of this complex of active agents on kallikrein 5 (KLK5) and cathelicidin (LL37) gene expression induced by a vitamin D analogue (calcitriol) in keratinocytes.

Materials and Methods

Normal human epidermal keratinocytes (NHEK) were cultivated in culture medium supplemented with Ca++ in order to bring them to a state of differentiation.

The keratinocytes were treated for 24 hours with 0.05% (w/v) *Schisandra* peptides in the presence or absence of 10-7 M calcitriol (vitamin D analogue).

At the end of the treatment, the culture supernatants were eliminated and total RNA extracted using an extraction kit (RNeasy Mini Kit, Qiagen). Total RNA were then assayed in chips using the Experion™ system and the Experion RNA StdSens kit (Bio-Rad) and then reverse-transcribed into cDNA using the iScript cDNA Synthesis kit (Bio-Rad).

The neo-synthesized cDNA relating to the genes of interest (KLK5 and LL37) or to the reference genes were amplified selectively by real-time PCR on an iQ5 system (Bio-Rad) using SybrGreen technology (iQ SybrGreen kit, Bio-Rad).

The real-time RT-PCR method enables the relative quantification of the expression level of a gene of interest in relation to that of a reference gene in response to a given treatment.

The quantitative analysis of the results is based on the collection of threshold cycles.

The threshold cycle (Ct) is the point at which the fluorescence emission signal is statistically and significantly higher than the background. The threshold cycle is directly correlated with the initial number of copies of target DNA.

For each sample, the expression level of the gene of interest was normalized by the expression level of the most stable reference gene. The most stable reference gene was determined using the GeNorm macro; in this case, it is the GAPDH gene.

$\Delta Ct$ is thus calculated as follows:

$$\Delta Ct = Ct_{target\ gene} - Ct_{reference\ gene}$$

In a second step, the variation, as a function of the treatment and the number of copies of the gene of interest, was determined. $\Delta\Delta Ct$ is thus calculated as follows:

$$\Delta\Delta Ct = \Delta Ct_{control} - \Delta Ct_{treated}$$

Lastly, relative quantity (RQ) is calculated: $RQ=(1+E)^{\Delta\Delta Ct}$.

E (efficiency) is considered equal to 1, and thus:

$$RQ = 2^{\Delta\Delta Ct}$$

The significance of the results was verified for the $\Delta Ct$ values by a single-factor analysis of variance followed by a Tukey's test (GraphPad Prism version 5.02 software, GraphPad Software, San Diego, Calif., USA).

Results

KLK5 Gene Expression:

Calcitriol (vitamin D analogue) strongly and significantly stimulated kallikrein 5 gene expression by the keratinocytes (+149%, p<0.01).

Schisandra peptides significantly inhibited the KLK5 expression induced by calcitriol (54% inhibition, p<0.01).

| | Mean ΔCt (CtKLK5 − CtGAPDH) | Standard deviation | ΔΔCt | KLK5 expression (RQ) |
|---|---|---|---|---|
| Control cells | 3.78 | 0.99 | 0.00 | 1 |
| Stimulated control (calcitriol) | 2.46 | 1.35 | 1.32 | 2.49$$ |
| 0.05% Schisandra peptides + calcitriol | 3.57 | 0.63 | 0.21 | 1.16** |

$$p < 0.01 vs. control cells
**p < 0.01 vs. stimulated control

LL37 Gene Expression:

Calcitriol strongly and significantly stimulated LL37 gene expression by the keratinocytes (+795%, p<0.001).

Schisandra peptides significantly inhibited the LL37 expression induced by calcitriol (58% inhibition, p<0.01).

| | Mean ΔCt (CtLL37 − CtGAPDH) | Standard deviation | ΔΔCt | LL37 expression (RQ) |
|---|---|---|---|---|
| Control cells | 14.17 | 0.69 | 0.00 | 1 |
| Stimulated control (calcitriol) | 11.01 | 0.28 | 3.16 | 8.95$$$ |
| 0.05% Schisandra peptides + calcitriol | 12.27 | 1.02 | 1.90 | 3.74** |

$$$p < 0.001 vs. control cells
**p < 0.01 vs. stimulated control

Conclusion

Under these experimental conditions, Schisandra peptides modulated the expression of a marker that is increased in rosacea, cathelicidin (LL37), as well as the enzyme responsible for its maturation, kallikrein 5.

Thus, Schisandra peptides can help modulate the induction of the inflammatory response in rosacea.

Example 4

Activity of a Schisandra sphenanthera Peptide and Sugar Extract on Other Parameters of Inflammation Materials and Methods Normal human keratinocytes were preincubated for 24 hours with Schisandra peptides at concentrations of 0.005% and 0.05% or with $10^{-7}$ M dexamethasone (anti-inflammatory reference molecule).

Inflammation was then induced by treatment with 10 μg/ml PMA for 24 hours, always in the presence of Schisandra peptides or dexamethasone.

At the end of incubation, the quantities of interleukin-1β (IL-1β), interleukin-8 (IL-8) and interleukin-6 (IL-6) present in the culture supernatants were measured by ELISA.

In parallel, the number of biologically active cells is determined by a neutral red test. The quantity of cytokine assayed for each condition is reduced to the number of living cells by dividing by the OD540 value obtained at the end of the neutral red test.

The significance of the results was verified by a single-factor analysis of variance followed by a Tukey's test (GraphPad Prism version 5.02 software, GraphPad Software, San Diego, Calif., USA).

Results

IL-1β secretion:

Treatment with PMA clearly stimulated the release of IL-1β by the keratinocytes and dexamethasone clearly inhibited this release (−65%); these results validate the test.

Schisandra peptides significantly inhibited IL-1β secretion induced by PMA in the keratinocytes at both concentrations tested: 64% inhibition (p<0.001) at 0.005% and 56% inhibition (p<0.001) at 0.05%.

| | IL-1β (ODELISA-ODneutral red) | |
|---|---|---|
| Control cells | 0.049 ± 0.008 | |
| Stimulated control (PMA) | 0.106 ± 0.008 | $$$ |
| $10^{-7}$ M dexamethasone | 0.037 ± 0.011 | −65%*** |
| 0.005% Schisandra peptides | 0.039 ± 0.001 | −64%*** |
| 0.05% Schisandra peptides | 0.047 ± 0.009 | −56%*** |

$$$ p < 0.001 vs. control cells
***p < 0.001 vs. stimulated control

IL-8 Secretion:

Treatment with PMA clearly stimulated the release of IL-8 by the keratinocytes and dexamethasone clearly inhibited this release (−53%); these results validate the test.

Schisandra peptides significantly inhibited the release of IL-8 induced by PMA at both concentrations tested: 58% inhibition (p<0.001) at 0.005% and 37% inhibition (p<0.001) at 0.05%.

| | IL-8 (pg/ml/ODneutral red) | |
|---|---|---|
| Control cells | 0.515 ± 0.080 | |
| Stimulated control (PMA) | 2.056 ± 0.166 | $$$ |
| $10^{-7}$ M dexamethasone | 0.973 ± 0.213 | −53%*** |
| 0.005% Schisandra peptides | 0.871 ± 0.032 | −58%*** |
| 0.05% Schisandra peptides | 1.285 ± 0.159 | −37%*** |

$$$ p < 0.001 vs. control cells
***p < 0.001 vs. stimulated control

IL-6 Secretion:

Treatment with PMA significantly induced the secretion of IL-6 by the keratinocytes and dexamethasone inhibited this release; these results validate the test.

Schisandra peptides strongly and significantly inhibited the release of IL-6 induced by PMA at both concentrations tested: −70% (p<0.001) at 0.005% and −74% (p<0.001) at 0.05%.

| | IL-6 (ODELISA/ODneutral red) | |
|---|---|---|
| Control cells | 0.069 ± 0.003 | |
| Stimulated control (PMA) | 0.098 ± 0.002 | $$ |
| $10^{-7}$ M dexamethasone | 0.043 ± 0.012 | −56%*** |
| 0.005% Schisandra peptides | 0.029 ± 0.003 | −70%*** |
| 0.05% Schisandra peptides | 0.025 ± 0.004 | −74%*** |

$$ p < 0.01 vs. control cells
***p < 0.001 vs. stimulated control

Conclusion

Under these experimental conditions, *Schisandra* peptides exhibited an inflammation modulating effect on a primary cytokine (IL-1β) and two secondary cytokines (IL-8 and IL-6).

Example 5

Activity of a *Schisandra sphenanthera* Peptide and Sugar Extract on Vascular Parameters 5.1. Limitation of Endothelial Cell Proliferation
Materials and Methods Normal human dermal microvascular endothelial cells were incubated for 24 or 48 hours in the absence (control) or presence of *Schisandra* peptides at concentrations of 0.05% and 0.1% and in the presence and absence of 10 ng/ml vascular endothelial growth factor (VEGF), the reference activator.

At the end of incubation, cell viability was evaluated by a spectrophotometric assay of intracellular phosphatase activity.

Statistical significance was evaluated by a single-factor analysis of variance followed by a Holm-Sidak test.
Results
Endothelial Cell Proliferation in the Absence of VEGF:

In baseline conditions (without VEGF), endothelial cell growth was significantly decreased after 24 hours of treatment with *Schisandra* peptides at both concentrations tested:

| 24 hours | 0.05% *Schisandra* peptides | −89.1% (p < 0.05) |
|---|---|---|
| | 0.1% *Schisandra* peptides | −112.7% (p < 0.05) |

Endothelial Cell Proliferation in the Presence of VEGF:

VEGF significantly stimulated endothelial cell growth in relation to control cells: +41.4% (p<0.01) after 24 hours of incubation and +96.3% (p<0.01) after 48 hours of incubation. This result validates the test.

*Schisandra* peptides, at both concentrations tested, significantly inhibited endothelial cell proliferation induced by VEGF:

| 24 hours | 0.05% *Schisandra* peptides | −51.8% (p < 0.05) |
|---|---|---|
| | 0.1% *Schisandra* peptides | −81.8% (p < 0.05) |
| 48 hours | 0.05% *Schisandra* peptides | −21.6% (p < 0.05) |
| | 0.1% *Schisandra* peptides | −27.1% (p < 0.05) |

Conclusion

*Schisandra* peptides, by limiting endothelial cell proliferation, can limit the early phase of angiogenesis.

5.2. Effect on the Expression of Angiogenesis Markers in Keratinocytes

In order to understand the antiangiogenic effect of *Schisandra* peptides, expression in keratinocytes of certain gene or protein markers involved in angiogenesis was studied, in particular expression of proangiogenic growth factors VEGF and FGF-2 and an antiangiogenic marker, thrombospondin-1 (THBS-1).

A. Expression of Proangiogenic Marker (VEGF, FGF-2) Genes
Materials and Methods

Normal human epidermal keratinocytes (NHEK) were incubated for 48 hours in the presence of 0.05% and 0.1% (w/v) *Schisandra* peptides.

At the end of the treatment, the culture supernatants were eliminated and total RNA extracted using an extraction kit (RNeasy Mini Kit, Qiagen). Total RNA were then assayed in chips using the Experion™ system and the Experion RNA StdSens kit (Bio-Rad) and then reverse-transcribed into cDNA using the iScript cDNA Synthesis kit (Bio-Rad).

The neo-synthesized cDNA relating to the genes of interest (VEGF, FGF-2, HIF-1α, THBS-1) or to the reference genes were amplified selectively by real-time PCR on an iQ5 system (Bio-Rad) using SybrGreen technology (iQ SybrGreen kit, Bio-Rad).

The real-time RT-PCR method enables the relative quantification of the expression level of a gene of interest in relation to that of a reference gene in response to a given treatment.

The quantitative analysis of the results is based on the collection of threshold cycles.

The threshold cycle (Ct) is the point at which the fluorescence emission signal is statistically and significantly higher than the background. The threshold cycle is directly correlated with the initial number of copies of target DNA.

For each sample, the expression level of the gene of interest was normalized by the expression level of the most stable reference gene. The most stable reference gene was determined using the GeNorm macro; in this case, it is the YWHAZ gene.

ΔCt is thus calculated as follows:

$$\Delta Ct = Ct_{target\ gene} - Ct_{reference\ gene}$$

In a second step, the variation, as a function of the treatment and the number of copies of the gene of interest, was determined. ΔΔCt is thus calculated as follows:

$$\Delta\Delta Ct = \Delta Ct_{control} - \Delta Ct_{treated}$$

Lastly, relative quantity (RQ) is calculated: RQ=(1+E)ΔΔCt.

E (efficiency) is considered equal to 1, and thus:

$$RQ = 2^{\Delta\Delta Ct}$$

The significance of the results was verified for the ΔCt values by a single-factor analysis of variance followed by a Dunnett's test (GraphPad Prism version 5.02 software, GraphPad Software, San Diego, Calif., USA).
Results Vascular Endothelial Growth Factor (VEGF) Gene Expression:

*Schisandra* peptides very strongly and significantly inhibited VEGF gene expression by the keratinocytes at both concentrations tested: 89% inhibition (p<0.001) at 0.05% and 93% inhibition (p<0.001) at 0.1%.

| | Mean ΔCt (CtVEGF − CtYWHAZ) | Standard deviation | ΔΔCt | VEGF expression (RQ) |
|---|---|---|---|---|
| Control cells | 8.41 | 2.09 | 0.00 | 1 |
| 0.05% *Schisandra* peptides | 11.63 | 2.91 | −3.23 | 0.107*** |
| 0.1% *Schisandra* peptides | 12.21 | 2.60 | −3.80 | 0.072*** |

***p < 0.001 vs. control cells

Basic Fibroblast Growth Factor (FGF-2) Gene Expression:

*Schisandra* peptides very strongly and significantly inhibited FGF-2 expression by the keratinocytes at both concentrations tested: 93% inhibition ($p<0.001$) at 0.05% and 95% inhibition ($p<0.001$) at 0.1%.

|  | Mean ΔCt (CtFGF-2 – CtYWHAZ) | Standard deviation | ΔΔCt | FGF-2 gene expression (RQ) |
|---|---|---|---|---|
| Control cells | 4.57 | 0.46 | 0.00 | 1 |
| 0.05% *Schisandra* peptides | 8.31 | 0.83 | −3.75 | 0.075*** |
| 0.1% *Schisandra* peptides | 8.86 | 1.00 | −4.30 | 0.051*** |

***$p < 0.001$ vs. control cells

Thrombospondin-1 Gene Expression:

*Schisandra* peptides significantly stimulated the expression of thrombospondin-1, an antiangiogenic factor, by the keratinocytes at both concentrations tested: +118% ($p<0.01$) at 0.05% and +60% ($p<0.05$) at 0.1%.

|  | Mean ΔCt (CtTHBS-1 – CtYWHAZ) | Standard deviation | ΔΔCt | THBS-1 expression (RQ) |
|---|---|---|---|---|
| Control cells | −0.85 | 0.19 | 0.00 | 1 |
| 0.05% *Schisandra* peptides | −1.98 | 0.50 | 1.13 | 2.181** |
| 0.1% *Schisandra* peptides | −1.54 | 0.51 | 0.68 | 1.605* |

*$p < 0.05$ vs. control cells
**$p < 0.01$ vs. control cells

B. Expression of an Angiogenesis Marker Protein (VEGF)

Material and Methods

Normal human keratinocytes were preincubated for 24 hours with *Schisandra* peptides at concentrations of 0.005%, 0.05% and 0.1% or with 10-7 M dexamethasone (anti-inflammatory reference molecule).

Inflammation was then induced by treatment with 10 µg/ml PMA for 24 hours, always in the presence of *Schisandra* peptides or dexamethasone.

At the end of incubation, the quantity of VEGF present in the culture supernatants was measured by ELISA.

In parallel, the number of biologically active cells is determined by a neutral red test. The quantity of cytokine assayed for each condition is reduced to the number of living cells by dividing by the OD540 value obtained at the end of the neutral red test.

The significance of the results was verified by a single-factor analysis of variance followed by a Tukey's test (GraphPad Prism version 5.02 software, GraphPad Software, San Diego, Calif., USA).

Results

Treatment with PMA significantly induced VEGF secretion by the keratinocytes and dexamethasone inhibited this release (−46%); these results validate the test.

*Schisandra* peptides strongly and significantly inhibited the VEGF release induced by PMA at the three concentrations tested: 63%, 72% and 69% inhibition ($p<0.001$), respectively.

|  | VEGF (pg/ml/ODneutral red) | |
|---|---|---|
| Control cells | 2521.921 ± 317.263 | |
| Stimulated control (PMA) | 3333.861 ± 111.766 | $ |
| 10⁻⁷ M dexamethasone | 1789.338 ± 489.677 | −46%*** |
| 0.005% *Schisandra* peptides | 1230.425 ± 35.305 | −63%*** |
| 0.05% *Schisandra* peptides | 928.914 ± 106.597 | −72%*** |
| 0.1% *Schisandra* peptides | 1027.362 ± 34.258 | −69%*** |

$ $p < 0.05$ vs. control cells
***$p < 0.001$ vs. stimulated control

C. Conclusion

Under the experimental conditions presented above, we demonstrated that *Schisandra* peptides modulated in keratinocytes the expression of factors involved in the induction of angiogenesis, and thus have an antiangiogenic effect.

Indeed, *Schisandra* peptides decreased the expression of proangiogenic markers (FGF-2, VEGF) and increased the expression of an antiangiogenic marker (THBS-1).

Thus by suppressing angiogenesis, an early phenomenon of neovascularization, *Schisandra* peptides can limit the activation of endothelial cells and the synthesis of new blood vessels.

5.3. Effect on Vasodilatation: Expression of Endothelin-1

Endothelin is a neuropeptide with powerful vasoconstrictive activity. It is secreted by endothelial and epithelial cells (keratinocytes), fibroblasts, adipocytes and macrophages. The effect of *Schisandra* peptides on endothelin production by endothelial cells was studied.

Materials and Methods

Normal adult human dermal microvascular endothelial cells cultivated in a monolayer were incubated for 6 hours in the absence (control) or the presence of 0.05% and 0.1% *Schisandra* peptides or 16.7 nM insulin (reference activator).

At the end of the incubation period, secreted endothelin was quantified by ELISA. In parallel, the proteins contained in the cellular lysates were quantified by the Bradford method.

The quantity of endothelin assayed was thus normalized with the quantity of total proteins, and the results were then expressed as the ratio of endothelin (ng) to total protein (µg) in the layer of cells.

The statistical significance of the results was evaluated by a single-factor analysis of variance followed by a Holm-Sidak test.

Results

*Schisandra* peptides significantly increased endothelin production by the endothelial cells at both concentrations tested: +67% ($p<0.05$) at 0.05% and +78% ($p<0.05$) at 0.1%.

|  | Endothelin (ng/µg of proteins) | |
|---|---|---|
| Control cells | 1.33 ± 0.11 | |
| 16.7 nM insulin | 1.72 ± 0.23 | +30% |
| 0.05% *Schisandra* peptides | 2.22 ± 0.27 | +67%* |
| 0.1% *Schisandra* peptides | 2.36 ± 0.15 | +78%* |

*$p < 0.05$ vs. control cells

Conclusion

By an effect on the expression of endothelin activation, *Schisandra* peptides can have a regulating effect on vasodilatation and thus reduce cutaneous redness.

The invention claimed is:

1. A cosmetic, dermatological or nutraceutical composition comprising a *Schisandra sphenanthera* fruit peptide and sugar extract, wherein said peptide and sugar extract comprises 10% to 50% by weight of peptides and 10% to 60% by weight of sugars.

2. A cosmetic, dermatological or nutraceutical composition according to claim 1, comprising at least one other active compound in addition to the *Schisandra sphenanthera* fruit peptide and sugar extract.

3. A cosmetic, dermatological or nutraceutical composition according to claim 1, comprising at least two *Schisandra sphenanthera* fruit extracts.

4. A method for treating allergic, inflammatory or irritative reactions or pathologies, or disorders of the barrier or the homeostasis of the skin and/or the mucosa and/or of immature, normal or mature/aged epithelial appendages, comprising administrating to a patient in need thereof the composition according to claim 1.

5. A method for treating cutaneous redness, erythrocouperose and rosacea comprising administrating to a patient in need thereof the composition according to claim 1.

* * * * *